United States Patent [19]

Burgin et al.

[11] Patent Number: 5,038,431
[45] Date of Patent: Aug. 13, 1991

[54] PILLOW CONSTRUCTION AND MEDICATION DISPENSER

[76] Inventors: Kermit H. Burgin, R.R. #1 - Box 334, Whitestown, Ind. 46075; R. Katheryn Echelbarger, Box 112, Zionsville, Ind. 46077

[21] Appl. No.: 100,423
[22] Filed: Sep. 24, 1987
[51] Int. Cl.$^5$ .............................................. A47C 20/00
[52] U.S. Cl. .................................... 5/438; 128/202.18
[58] Field of Search ................... 5/438, 434, 457, 449, 5/442; 128/202.18; 220/360, 361, 253

[56] References Cited

U.S. PATENT DOCUMENTS

| | | | |
|---|---|---|---|
| 233,954 | 11/1880 | Thompson | 5/438 X |
| 290,608 | 12/1883 | Snyder | 128/202.18 |
| 618,210 | 1/1899 | Shakespeare | 128/202.18 |
| 1,777,982 | 10/1930 | Popp . | |
| 1,876,591 | 9/1932 | Bawden | 5/438 |
| 2,162,999 | 6/1939 | Frank | 220/253 X |
| 2,305,173 | 12/1942 | Leeb | 5/438 |
| 2,500,974 | 3/1950 | Angert | 5/442 |
| 4,277,859 | 7/1981 | Seaman . | |
| 4,607,403 | 8/1986 | Alivizatos | 5/449 |

FOREIGN PATENT DOCUMENTS

| | | | |
|---|---|---|---|
| 473604 | 3/1929 | Fed. Rep. of Germany | 5/438 |
| 780514 | 4/1935 | France | 5/438 |

Primary Examiner—David L. Talbott
Attorney, Agent, or Firm—Barnes & Thornburg

[57] ABSTRACT

A pillow includes an outer sheet which forms a pocket to receive a filling material. The sheet is substantially impermeable to the filling material and is formed to include at least one vent opening. A cover having an opening therein is disposed over the vent opening. A cover having an opening therein is disposed over the vent opening. The cover is movable between a first orientation in which the vent opening and the opening in the cover are out of alignment and a second orientation in which the vent opening and the opening in the cover are in alignment. The filling material is impregnated with a medicament or the like to expose a person or animal resting on the pillow to the medicament through the vent opening.

13 Claims, 1 Drawing Sheet

PILLOW CONSTRUCTION AND MEDICATION DISPENSER

This invention relates to pillow constructions and particularly to a pillow construction which can be achieved economically and which permits a medication-dispensing capability to be incorporated into the pillow.

It is an object of the invention to provide an economical pillow construction.

It is a further object of the present invention to provide a pillow construction which enhances the transport of medication from a source of medication to the person or animal resting on the pillow.

According to the invention, a pillow, cushion or the like, comprises a sheet forming a pocket, and means for stuffing the pocket. The sheet is substantially impermeable to the stuffing means. The sheet includes means defining a vent opening. A cover is provided for the vent opening, along with means for mounting the cover movably relative to the vent opening. The cover includes means defining an opening in it. The means for mounting the cover permits movement of the cover between an orientation in which the vent opening and the opening in the cover are out of alignment and a second orientation in which the vent opening and the opening in the cover are in alignment.

Additionally according to the invention, the pillow further comprises means defining a second vent opening, a second cover for the second vent opening, and means for mounting the second cover movably relative to the second vent opening. The second cover includes means defining an opening. The second cover is movable between a first orientation in which the second vent opening and the opening in the second cover are out of alignment and a second orientation in which the second vent opening and the opening in the second cover are in alignment.

Further according to the invention, the cover and second cover are generally circular and the means for mounting the cover and second cover movably relative to the opening and second opening, respectively, comprise means for mounting the cover and second cover for rotation generally about their respective centers adjacent the vent opening and the second vent opening, respectively.

Alternatively, the cover and second cover are generally rectangular and the means for mounting the cover and the second cover movably relative to the opening and the second opening, respectively, comprise means for mounting the cover and the second cover slidably adjacent the vent opening and the second vent opening, respectively.

Additionally according to the invention, the means for stuffing the pocket comprises imgregnable particles. A medicament or the like is provided for impregnating the impregnable particles. Illustratively, the impregnable particles are expanded polystyrene particles, such as PELASPAN-PAK TM particles. The medicament can be a flea- or other parasite-treatment, camphor, or any other material which can be released through the vent openings to treat the person or animal resting on the pillow.

Additionally, illustratively, the pocket has a length dimension and a width dimension. The length dimension is larger than the width dimension. The sheet includes ribs, which in the pillow construction extend generally transverse to the length dimension and generally along the width dimension around the pocket and project into it.

The invention may best be understood by referring to the following description and accompanying drawings which illustrate the invention. In the drawings.

Figure 1:
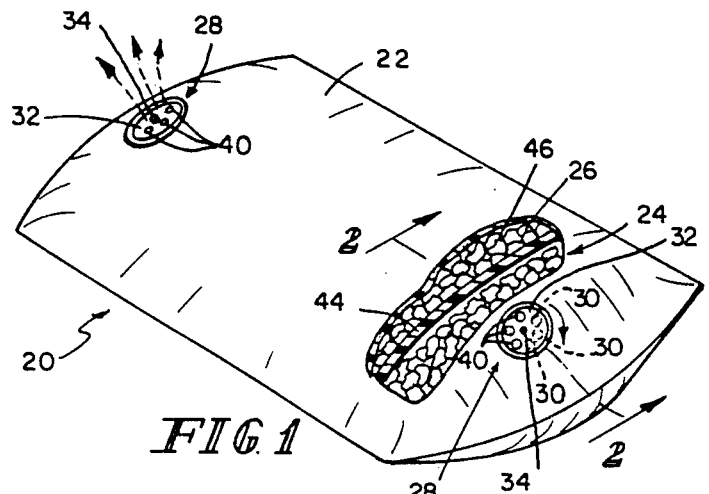
FIG. 1 illustrates a partly fragmentary perspective view of a pillow, cushion, or the like constructed according to the present invention.

Turning to FIG. 1, a pillow, cushion or the like, 20, is constructed from a sheet 22 of material, such as a synthetic resinous material, to provide a pocket 24. Pocket 24 is stuffed, illustratively during the construction of pillow 20, with a material 26 to which sheet 22 is generally impervious. If the pillow 20 is constructed from two sheets of synthetic resinous material which are heat staked together about their perimeters, for example, this stuffing step can take place immediately prior to heat staking the last edges together. The illustrative stuffing material 26 is PELASPAN-PAK TM, an expanded polystyrene material available from Dow Chemical Company. Prior to stuffing the pocket, the stuffing material 26 itself is impregnated with, or otherwise treated to serve as a carrier for, a volatile or air-entrainable medicament or the like with which the person or animal who or which is going to use the pillow 20 is to be treated. Examples of such materials are camphor and various parasite treatment compositions, such as flea powders and the like.

In order to provide passage through the sheet 22 for the medicament, vents 28 are provided in the sheet 22. Each vent 28 includes a vent opening 30 which is circular in the embodiment illustrated in FIG. 1. Each vent 28 further includes a cover 32 which is movably mounted adjacent its respective vent opening 30. The illustrated covers 32 are generally circular and are mounted by rivets 34 which pass through small openings 36, 38 at approximately the centers of covers 32 and adjacent vent openings 30, respectively. The rivets 34 are then flattened at both ends to capture covers 32 rotatably adjacent their respective vent openings 30.

Each cover 32 is provided with multiple, illustratively three, openings 40. The openings 40 are illustratively circular, are spaced at regular intervals on covers 32, and are oriented with their centers at equal radii from openings 36. An equal plurality of vent openings 30, spaced in substantially the same way relative to openings 38, are provided at each vent 28. In this way, one or more of openings 40 of each cover 32 can be aligned with an equal number of vent openings 30 to increase or reduce, selectively, the release of medicament from pocket 24 as the person or animal resting on pillow 20 lies down on it and moves during rest on it. This movement, it will be noted, effectively pumps air into, and pumps air entraining the medicament out of, pocket 24.

The illustrative vent 28 can be constructed from a slightly thicker, yet pliable, synthetic resinous material than sheet 22. Illustratively polyvinyl chloride can be used for the region around vent opening 30 and for cover 32. Rivet 34 can be formed from a somewhat harder material, such as polystyrene, but an effort should be made to use as soft and pliable materials as possible throughout to promote user comfort. Rivet 34 is illustratively heat staked into openings 36, 38, and the region around vent opening 30 can be assembled into a circular hole in sheet 22, either before or after assembly of the vent 28, using a suitable adhesive.

Figure 2:
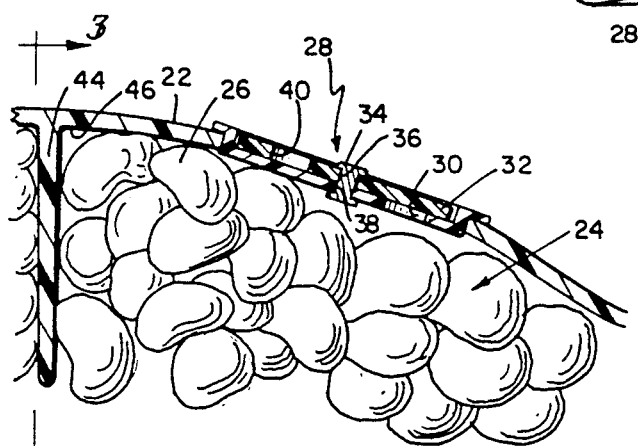
FIG. 2 illustrates an enlarged fragmentary sectional view taken generally along section lines 2—2 of FIG. 1.
Figure 3:
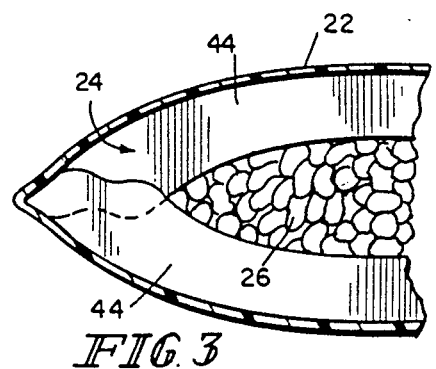
FIG. 3 illustrates an enlarged fragmentary sectional view taken generally along section lines 3—3 of FIG. 2.

As best illustrated in FIGS. 2-3, sheet 22 is provided with integrally formed ribs 44 at selected, illustratively regular, intervals along its surface 46. In the assembly of pillow 20, these ribs 44 are oriented to extend generally transversely to the length (longer) dimension of the pillow 20 and generally along the width (shorter) dimension of the pillow 20. These ribs 44 help reinforce the pillow 20 somewhat against excessive deformation.

Figure 5:
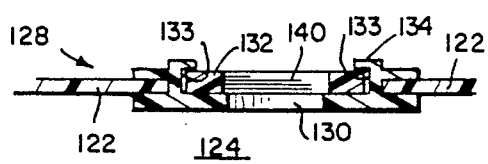
Figure 4:
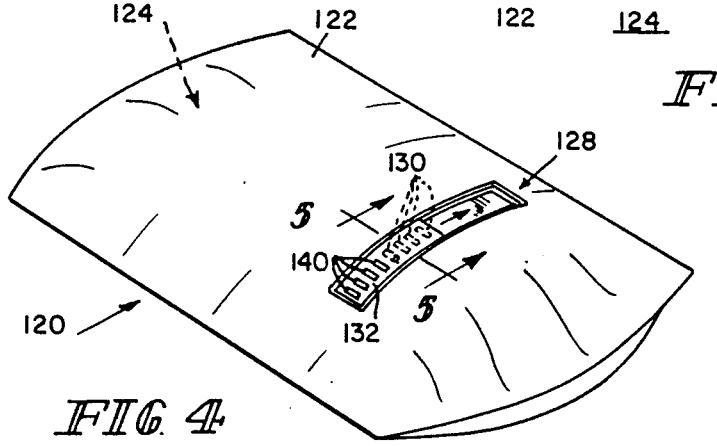
FIG. 4 illustrates a perspective view of another pillow, cushion, or the like constructed according to the present invention; and, FIG. 5 illustrates an enlarged fragmentary sectional view taken generally along section lines 5—5 of FIG. 4.

In the embodiment of the invention illustrated in FIGS. 4-5, a vent 128 is provided in the sheet 122 from which the pillow 120 is constructed. Vent 128 includes vent openings 130 which are rectangular slot-shaped in the embodiment illustrated in FIGS. 4-5. Vent 128 further includes a cover 132 which is slidable adjacent its respective vent opening 130. The illustrated cover 132 is generally rectangular and is slidable in C-shaped channels 133 provided at the longitudinal edges of an insert 134 in which vent openings 130 are provided.

Cover 132 is provided with three openings 140. The openings 140 are rectangular slot-shaped, and are shaped at regular intervals in cover 132. An equal plurality of vent openings 130, spaced in substantially the same way as openings 140, are provided at vent 128. In this way, one or more of openings 140 of cover 132 can be aligned with an equal number of vent openings 130 to increase or reduce, selectively, the release of medicament from pocket 124 as the person or animal resting on pillow 120 lies down on it and moves during rest on it.

The illustrative vent 128 can be constructed from a slightly thicker, yet pliable, synthetic resinous material than sheet 122. Illustratively, polyvinyl chloride can be used for the insert 134 and for cover 132. Insert 134 can be assembled into a rectangular hole in the sheet 122 from which pillow 120 is formed, either before or after assembly of the vent 128, using a suitable adhesive.

What is claimed is:

1. A pillow, cushion, or the like comprising a sheet forming a pocket, means for filling the pocket, the sheet being substantially impermeable to the means for filling the pocket, the sheet including means defining a vent opening, a cover for the vent opening, and means for mounting the cover movably relative to the opening, the cover including means defining an opening, the cover being movable between a first orientation in which the vent opening and the opening in the cover are out of alignment and a second orientation in which the vent opening and the opening in the cover are in alignment, the means for filling the pocket comprising impregnable particles, and the apparatus further comprising a medicament or the like for impregnating the impregnable particles.

2. The apparatus of claim 1 and further comprising means defining a second vent opening, a second cover for the second vent opening and means for mounting the second cover movably relative to the second vent opening, the second cover including means defining an opening, the second cover being movable between a first orientation in which the second vent opening and the opening in the second cover are out of alignment and a second orientation in which the second vent opening and the opening in the second cover are in alignment.

3. The apparatus of claim 2 wherein the cover and the second cover are generally circular and the means for mounting the cover and the second cover movably relative to the opening and the second opening, respectively, comprise means for mounting the cover and the second cover for rotation generally about their respective centers adjacent the vent opening and the second vent opening, respectively.

4. The apparatus of claim 2 wherein the cover and the second cover are generally rectangular and the means for mounting the cover and the second cover movably relative to the opening and the second opening, respectively, comprise means for mounting the cover and the second cover slidably adjacent the vent opening and the second vent opening, respectively.

5. The apparatus of claim 1 wherein the cover is generally circular and the means for mounting the cover movably relative to the opening comprises means for mounting the cover for rotation generally about its center adjacent the vent opening.

6. The apparatus of claim 1 wherein the impregnable particles comprise expanded polystyrene particles.

7. The apparatus of claim 1 having a length dimension and a width dimension, the length dimension being larger than the width dimension, the sheet defining ribs which extend generally transverse to the length dimension and generally along the width dimension around the pocket and project into it.

8. A pillow, cushion, or the like comprising a sheet forming a pocket, means for filling the pocket, the sheet being substantially impermeable to the means for filling the pocket, the sheet including means defining a vent opening, a cover for the vent opening, and means for mounting the cover movably relative to the opening, the cover including means defining an opening, the cover being movable between a first orientation in which the vent opening and the opening in the cover are out of alignment and a second orientation in which the vent opening and the opening in the cover are in alignment, the cover being generally rectangular and the means for mounting the cover movably relative to the opening comprising means for mounting the cover slidably adjacent the vent opening.

9. The apparatus of claim 8 wherein the means for filling the pocket comprises impregnable particles, the apparatus further comprising a medicament or the like for impregnating the impregnable particles.

10. The apparatus of claim 9 wherein the impregnable particles comprise expanded polystyrene particles.

11. The apparatus of claim 8 having a length dimension and a width dimension, the length dimension being larger than the width dimension, the sheet defining ribs which extend generally transverse to the length dimension and generally along the width dimension around the pocket and project into it.

12. The apparatus of claim 8 and further comprising means defining a second vent opening, a second cover for the second vent opening and means for mounting the second cover movably relative to the second vent opening, the second cover including means defining an opening, the second cover being movable between a first orientation in which the second vent opening and the opening in the second cover are out of alignment and a second orientation in which the second vent opening and the opening in the second cover are in alignment.

13. The apparatus of claim 12 wherein the second cover is generally rectangular and the means for mounting the second cover movably relative to the second opening comprises means for mounting the second cover slidably adjacent the second vent opening.

* * * * *